(12) United States Patent
Bhatia

(10) Patent No.: US 6,831,181 B2
(45) Date of Patent: Dec. 14, 2004

(54) HIGH YIELD BYPRODUCT RECYCLE PROCESS FOR ANHYDRO SUGAR ALCOHOLS

(75) Inventor: Kamlesh Kumar Bhatia, Newark, DE (US)

(73) Assignee: E. I. Dupont de Nemours and Co., Wilmington, DE (US)

( * ) Notice: Subject to any disclaimer, the term of this patent is extended or adjusted under 35 U.S.C. 154(b) by 23 days.

(21) Appl. No.: 10/414,605

(22) Filed: Apr. 16, 2003

(65) Prior Publication Data

US 2003/0229235 A1 Dec. 11, 2003

Related U.S. Application Data

(60) Provisional application No. 60/373,210, filed on Apr. 17, 2002.

(51) Int. Cl.[7] ...................... C07D 307/02; C07D 493/00
(52) U.S. Cl. ........................ 549/464; 549/464; 549/476
(58) Field of Search ................................. 549/476, 464

(56) References Cited

U.S. PATENT DOCUMENTS

| | | |
|---|---|---|
| 4,564,692 A | 1/1986 | Feldmann et al. |
| 4,861,513 A * | 8/1989 | Lueders et al. ........ 252/182.24 |
| 6,407,266 B2 | 6/2002 | Bhatia |

FOREIGN PATENT DOCUMENTS

| | | |
|---|---|---|
| WO | WO 00/14081 | 3/2000 |
| WO | WO 00/41985 | 7/2000 |
| WO | WO 01/92246 | 12/2001 |
| WO | WO 02/36598 | 11/2003 |

OTHER PUBLICATIONS

Bock, et al., "Acid Catalyzed Dehydration of Alditols.PartI. d–Glucitol and d–Mannitol", Acta Chemica Scandinavica B 35 (1981), pp. 441–449 (Lyngby, Denmark).

Fleche, et al. "Preparation, Properties and Chemistry", starch/starke 38 (1986) pp. 26–30 (France).

Beck, Roland, "Pharm. Mfg. Inc." (1996), pp. 97–100.

* cited by examiner

*Primary Examiner*—Rita Desai
*Assistant Examiner*—Raymond Covington

(57) ABSTRACT

A process for recycling reaction byproducts in the manufacture of dianhydro sugar alcohols, such as isosorbide, from corresponding sugar alcohols.

13 Claims, 2 Drawing Sheets

HIGH YIELD BYPRODUCT RECYCLE PROCESS FOR ANHYDRO SUGAR ALCOHOLS

FIELD OF THE INVENTION

This invention concerns a process for separating and recycling reaction byproducts in the manufacture of dianhydro sugar alcohols.

TECHNICAL BACKGROUND OF THE INVENTION

Anhydro sugar alcohols, in particular derivatives of mannitol, iditol, and sorbitol, are known for their therapeutic uses and uses in food. At least one of these, isosorbide, 1,4:3,6-dianhydrosorbitol, is useful as a monomer used in the manufacture of polymers and copolymers, especially polyester polymers and copolymers.

Anhydro sugar alcohols are produced by dehydration of the corresponding sugar alcohols (or monoanhydro sugar alcohols) by the action of various dehydration catalysts, typically strong acid catalysts.

Batch processes for the preparation of dianhydro sugar alcohols by acid dehydration are known in the art.

In particular, a batch process for the formation of the dianhydro sugar alcohol isosorbide has been described as a two step process involving intramolecular dehydration of sorbitol to 1,4-sorbitan (1,4-monoanhydrosorbitol), and further reaction of the sorbitan to isosorbide (1,4:3,6-dianhydrosorbitol) in an acid catalyzed dehydration-cyclization. This reaction produces isosorbide and a higher molecular weight byproduct. The byproduct is presumably produced by water elimination between two or more sorbitol molecules, but its exact nature is not clearly defined. See G. Flèche and M. Huchette, Starch/Starke (1986), 38(c), 26–30 and Roland Beck, *Pharm. Mfg Inc.* (1996), 97–100. Other monoanhydro byproducts, 2,5-anhydro-L-iditol and 2,5-anhydro-D-mannitol, are also known to be produced under some reaction conditions (*Acta. Chem. Scand.* B 35, 441–449 (1981)).

WO 00/14081 describes a continuous process for producing anhydro sugar alcohols, especially isosorbide, comprising the steps of introducing at least one sugar alcohol or monoanhydro sugar alcohol into a reaction vessel; dehydrating the sugar alcohol or monoanhydro sugar alcohol in the presence of an acid catalyst and an organic solvent to form a reaction product which is at least partly soluble in the organic solvent; removing water from the reaction vessel; removing organic solvent comprising the dissolved reaction product from the reaction vessel; separating the reaction product from the removed organic solvent; and recycling the organic solvent into the reaction vessel.

U.S. Pat No. 6,407,266 describes a continuous process in which a process stream containing at least one sugar alcohol or monoanhydro sugar alcohol and, optionally, water is introduced to the first stage of a multistage reactor and then intimately contacted with a countercurrent flow of an inert gas at elevated temperature to remove the bulk of any water present to yield a dewatered process stream. This dewatered process stream is then intimately contacted with a counter current flow of an inert gas at elevated temperatures, in the presence of a dehydration catalyst, to remove water of reaction as formed. Finally, the reaction product is removed from the bottom of the reactor.

The reaction product of the above processes contains the desired dianhydro sugar alcohols and undesired byproducts as described above. The dianhydro sugar alcohols are isolated from the reaction mass by one or more purification steps such as evaporation, distillation, extraction and ion exchange or combinations thereof.

Commonly owned CL-1894, filed simultaneously herewith, teaches a continuous process for the manufacture and separation of dianhydro sugar alcohols, especially isosorbide, wherein, starting with an aqueous solution of sugar alcohol at a concentration of about 45%–50%, acid-catalyzed dehydration to form the dianhydro sugar alcohol is carried out in a single, multistage reaction-separation vessel, and separation of the dianhydro sugar alcohol from the reaction mass occurs simultaneously with the help of water vapor evolved. In the above processes, separation of dianhydro sugar alcohols from the reaction mass is not complete, and substantial quantities of product are lost with the higher boiling byproducts. Increasing the vaporization temperature may increase product recovery, but this adversely affects product quality, as more of the byproducts and color-forming impurities are vaporized along with the desired product. In the case of chromatographic separation, substantially larger equipment is required to achieve higher recovery, which may not be economical.

For isosorbide to be used as a monomer in high volume applications, such as polyester containers, there is a need for a continuous, high yield, high recovery, economical process for producing isosorbide.

The object of the present invention is to provide a process wherein the reaction byproducts and anhydro sugar alcohols not recovered initially from the reaction mass are recycled back to the reaction step and overall yield of the anhydro sugar alcohols, such as isosorbide, is increased.

SUMMARY OF THE INVENTION

This invention provides a process for separating monomeric and dimeric sugar alcohols from a mixture comprising monomeric, dimeric and polymeric sugar alcohols, comprising:

a) diluting with water a mixture comprising monomeric, dimeric and polymeric sugar alcohols;

b) allowing most of the polymeric sugar alcohols to precipitate from the diluted mixture obtained in (a); and c) separating the precipitated polymeric sugar alcohols from the diluted mixture to obtain a solution of soluble monomeric and dimeric sugar alcohols.

The process can be conducted in a batch, semi-batch, or continuous mode. It can also be conducted with an additional step of purging a portion of the soluble monomeric and dimeric sugar alcohols.

The process of this invention can be used to separate the generally more desirable monomeric and dimeric sugar alcohols from the higher molecular weight, polymeric sugar alcohols in a byproduct stream derived from the production of a dianhydro sugar alcohol via an acid-catalyzed dehydration of the corresponding sugar alcohol. The by-product stream is that portion of the reaction mass that remains after a portion of the desired dianhydro sugar alcohol has been removed from the reaction mass, e.g., by distillation or crystallization.

DETAILED DESCRIPTION OF THE INVENTION

Figure 1:
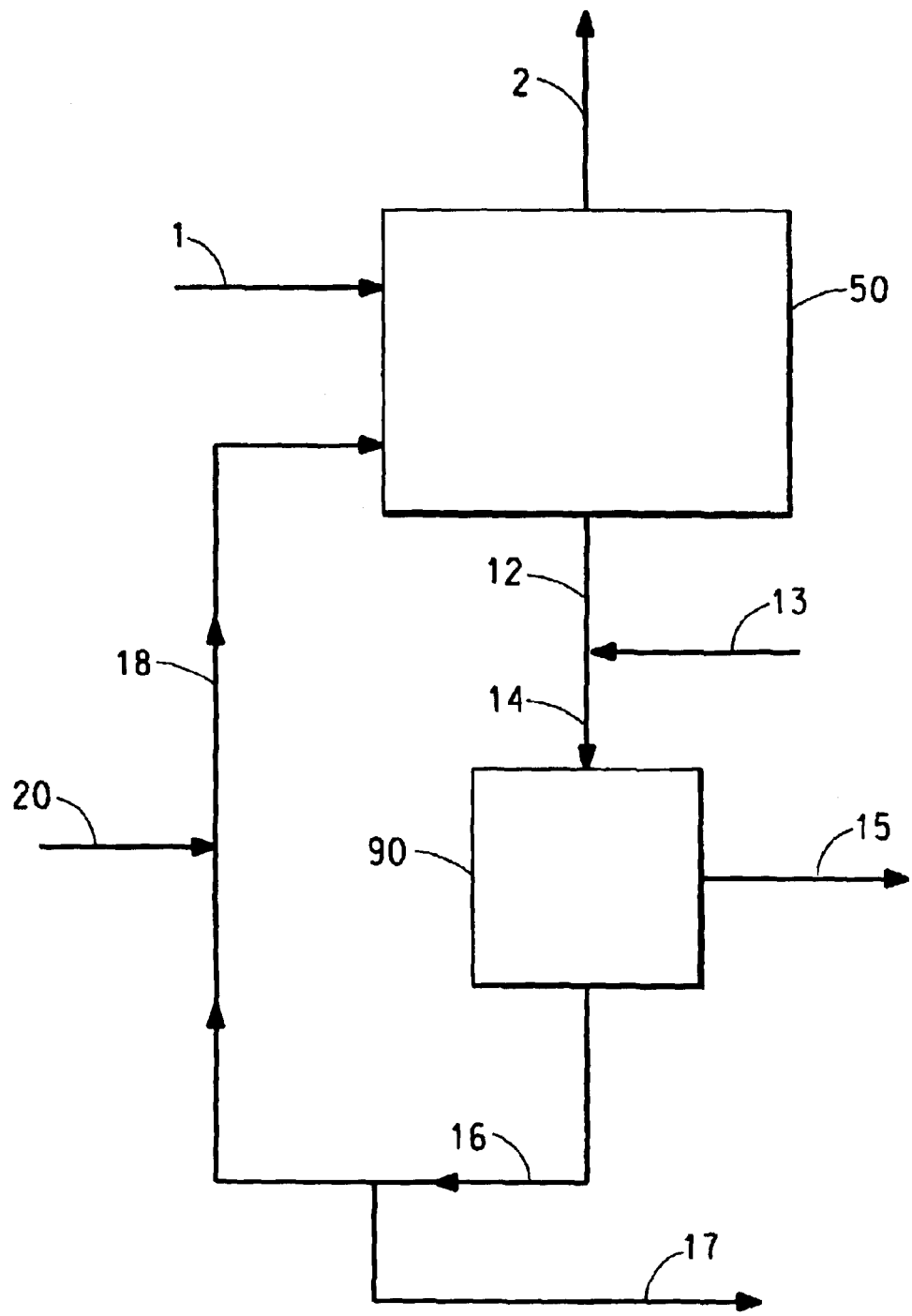
FIG. 1 is a schematic representation of a preferred embodiment of the process of the present invention.

The present disclosure provides a process for recycling reaction byproducts and unrecovered anhydro sugar alcohols that result from dehydration reaction and product separation steps in the manufacture of dianhydro sugar alcohols from the corresponding sugar alcohols.

Dehydration of sugar alcohols is generally conducted at elevated temperatures in the presence of an acid catalyst, such as hydrochloric acid or sulfuric acid. The dehydration reaction is believed to proceed in two steps: (1) dehydration of the sugar alcohols to monoanhydro sugar alcohols with the evolution of one mole of water for every mole of sugar alcohol, followed by (2) dehydration of the monoanhydro sugar alcohols to dianhydro sugar alcohols with the evolution of a second mole of water. The dehydration reactions are, however, accompanied by several side reactions that lead to generation of unwanted byproducts.

A typical sugar alcohol used in the above dehydration reaction is sorbitol, and the corresponding dianhydrosugar alcohol of interest is isosorbide. The reactions involved in the acid-catalyzed dehydration of sorbitol, the byproducts formed, and the problems encountered in separating the desired dianhydrosugar alcohol (isosorbide) from the reaction mixture are illustrative for the class of sugar alcohols, and will be described in some detail here. The process of this invention, also described in detail below for isosorbide, can also be used to separate and recycle byproducts formed in the acid catalyzed dehydration of other sugar alcohols to their corresponding dianhydrosugar alcohols.

In the dehydration of sorbitol to isosorbide, sorbitol first dehydrates to the various sorbitan isomers, namely 1,4-anhydro-D-glucitol (also known as 1,4-sorbitan); 3,6-anhydro-D-glucitol; 2,5-anhydro-D-mannitol; and 2,5-anhydro-L-iditol, all of which can be termed monomeric sugar alcohols. The 1,4 and 3,6 isomers dehydrate further to form isosorbide; the 2,5 isomers do not. As the dehydration reaction proceeds, various species present in the reaction mass, including sorbitol, the four monoanhydro isomers, and isosorbide, react with each other to form a number of different dimers, which then polymerize to form higher oligomers; these oligomers are referred to herein, as "polymeric sugar alcohols." In addition, the various species present undergo a host of other side reactions, which generate color-forming species, charred material, and various decomposition products.

The byproducts formed, comprising mostly the undesired monomeric monoanhydro sugar alcohols, dimers, and polymeric sugar alcohols, may constitute, at the completion of the dehydration reaction, about 20 to 30 weight % of the reaction mass, depending upon the reaction conditions. A yield loss of about 20 to 30% to byproducts is typical for the conversion of sorbitol to isosorbide at a reaction temperature of about 140° C. in the presence of sulfuric acid catalyst.

Recovery of the desired dianhydrosugar alcohol from the reaction mass is often difficult due to low volatility. For example, at about 140–145° C., the vapor pressure of isosorbide is only about 2 mm Hg.

Also, the solubility properties of the desired products may be similar to those of the byproducts. The solubility properties of isosorbide are similar to those of the sorbitan isomers, making it difficult to develop an economically effective separation by solvent extraction.

The sorbitans, dimers, and polymer byproducts are all considerably higher boiling than isosorbide. For example, the vapor pressure of the sorbitans is only about 0.04 mm Hg at 140° C., about one-fiftieth that of isosorbide. As described in the art, recovery of isosorbide from the reaction mass by vaporization or distillation can be employed, generally after neutralizing the acid catalyst to avoid product degradation at the elevated distillation temperatures. Product recovery, however, is far from complete, and a substantial quantity of the product, 20 to 30%, may be lost as unrecovered with the byproducts, particularly when recovering a product of good purity. For example, when isosorbide is volatilized from a reaction mass containing 20 to 30% high boiling byproducts at about 140–145° C. under high vacuum (e.g., 1 mm Hg pressure), it leaves unrecovered isosorbide with the byproducts in an amount equal to that of the byproducts. Thus, about 20–30% of the byproducts plus 20–30% isosorbide present in the reaction mass remain as the unvolatilized high-boiling bottoms in the byproduct stream, and overall yield of isosorbide, after reaction and separation, is only 40–60%. Recovery can be improved by subjecting the byproduct stream to higher temperatures and/or still lower pressures, but that is at the expense of higher degradation and poorer quality product. Another practical limitation is that above 170° C., the reaction mass starts to char at a rapid rate.

In the process of the present invention, the unrecovered dianhydrosugar alcohol and the other monomeric and dimeric sugar alcohols are separated from the other byproducts and can be recycled back to the dehydration reaction step in the manufacturing process, providing higher overall recovery without resorting to higher temperatures. This separation is effected by diluting the byproduct stream with water and allowing the polymeric sugar alcohols to precipitate. The monomeric and dimeric sugar alcohols remain in solution, and can be separated from the precipitated polymers and recycled.

A preferred embodiment of the process of the present invention is described below and illustrated schematically in FIG. 1.

Referring to FIG. 1, block (50) represents the equipment for conducting the dehydration reaction and separating the product dianhydro sugar alcohols from the reaction mass. These steps may be conducted by any one of the processes disclosed in the prior art or by the simultaneous reaction-separation process disclosed by Bhatia (copending U.S. Provisional Application No. 60/373,106, filed concurrently). The simultaneous reaction-separation process is preferred, as it does not require neutralization of the acid catalyst, and, as described below, the acid catalyst also gets recycled.

Line (1) represents the sugar alcohol (e.g., sorbitol) feed to the reactor. Line (2) represents the dianhydro sugar alcohol product, isosorbide, recovered from the reaction mass. Line (12) represents the high boilers, i.e., the reaction byproducts and unrecovered dianhydro sugar alcohol (e.g., isosorbide). The high boilers (12) are diluted with cooling water via line (13) in amount sufficient to precipitate most of the polymers from the solution. The quantity of water is at least equal to that of the high boilers (wt/wt). Preferably, the water added is about 2 lbs water/lb of high boilers. Addition of large quantities of water, however, is not necessary and not desirable as it increases the water load on the equipment. Therefore, it is preferred that the water added is not greater than 4 lbs/lb of high boilers. The water may be mixed with the high boilers by any means known in the art, for example, a stirred mixing vessel, an inline mixer, or simply a mixing tee. These are not explicitly shown in FIG. 1. Dilution of the high boilers with water at ambient temperature reduces the acid concentration and cools the high boilers. Under these conditions, the polymer present in the high boilers starts to precipitate.

Optionally, the acid concentration may be reduced by neutralizing it with a suitable base, preferably an inexpensive inorganic hydroxide that reacts with the acid to form an insoluble salt. Another option is to let the diluted mixture cool further by heat loss to the atmosphere or, for ease in further handling, by cooling in a heat exchanger. These options can result in more complete precipitation of the polymer and reduce the water load and the load on further processing equipment.

The mixture of high boilers and water is fed to a solid-liquid separation device (90), via line (14), where the precipitated solids, comprising mostly polymeric sugar alcohols, are separated. This can be any suitable device known in the art, such as a filter or a centrifuge. The filter cake obtained in these devices is preferably subjected to a wash cycle with cooling water to wash away the acid and byproduct solution from the filter cake. The washed filter cake, represented by line (15), is then removed from device (90) and disposed of in a suitable manner. The liquid part, comprising a solution of the remaining dissolved byproducts, such as the monomeric monoanhydro alcohols, dimers and the unrecovered dianhydro sugar alcohol, is removed via line (16) for recycle back to the reactor via line (18).

The recycle solution may be injected into the reaction vessel in block (50) as a separate stream or as a mixture with fresh sugar alcohol feed added. Most of the acid catalyst also gets recycled back to the reactor, and catalyst consumption is thereby reduced considerably. Any acid catalyst lost in the process, for example, through a purge such as via line (17) as described below or through the optional neutralization, if employed, can be made up by injecting make up acid via line (20).

As the byproducts (i.e., the monomeric sugar alcohols and dimers) are recycled back to the reactor, their concentration starts to build up in the reaction mass. This causes their rate of consumption to form polymer to increase. After some time, or several recycles (in the case of batchwise operation), the process reaches steady state, i.e., the byproduct concentration remains constant, as the rate of newly formed byproduct species and dimers equals the rate of their disappearance to form polymer.

Thus, the byproduct recycle process of the present invention accomplishes removal of most of the byproducts formed in the dehydration reaction, as washed polymer via line (15), and recycles the dianhydrosugar alcohol not recovered in the initial separation step to increase overall recovery.

As described above, recycle of byproducts leads to higher concentration of byproducts in the reaction mass. Consequently, the dehydration reaction takes place under dilute conditions, i.e., lower concentration of the reacting species. Thus, the rate of dimer formation is reduced relative to the rate of formation of dianhydro sugar alcohol product. This results in a higher reaction yield of the desired product. The process of the present invention thus allows one to conduct the reaction under dilute conditions without introducing any new solvents into the reaction system and makes use of the reaction byproducts themselves to serve as a diluent.

In the process of the present invention, a portion of the byproducts solution from line (16) may be purged via line (17) to circumvent buildup of certain minor, not completely identified, water soluble byproducts, such as color forming species, in the reaction mass. The purge stream may be treated further to recover useful species, depending upon economics, or disposed of in a safe manner.

From the above detailed description of the process, it would be obvious to one skilled in-the art that the process could be conducted in a batchwise, intermittent, or continuous mode. Continuous operation is preferred for large-scale production. In continuous operation, the flows in process input lines (1), (13), (20); output lines (15), (17); and lines from one step to the next (12), (14), (16), (18) are maintained at a substantially steady rate and are coordinated to maintain substantially steady operating conditions.

Figure 2:
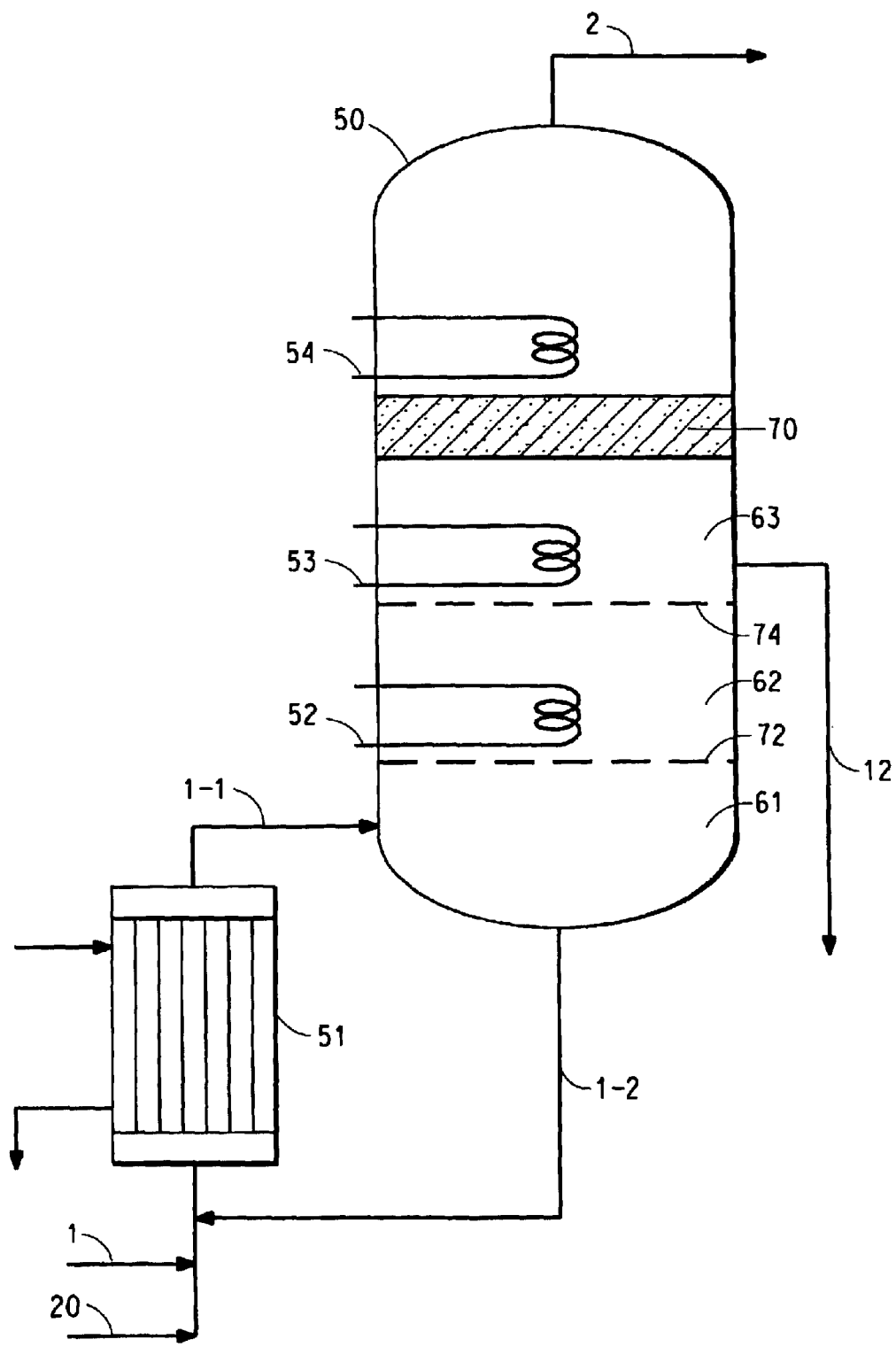
FIG. 2 is a schematic representation of the internal fittings of the reaction vessel.

FIG. 2 shows the internal fittings of FIG. 1. Dehydration takes place in the reaction vessel (50), which is fitted with sieve plates for multistage operation and equipped with heaters (51, 52, and 53). It is provided with input lines (1), (13) and (20) for starting materials, such as the aqueous solution of sugar alcohol and acid catalyst, as well as outlet lines for product vapor removal and high boilers removal.

Any means of heating may be employed to maintain the reaction vessel at the desired temperature. Internal steam coils for heaters (52) and (53) for stages 2 and 3, respectively, are schematically illustrated in FIG. 2. For the first stage, where most of the heat must be supplied in order to evaporate most of the water, an external heat exchanger (51) is selected for ease of fabrication. This heater is preferably a steam, shell and tube, heat exchanger that circulates the reaction mass through it with thermosyphon action. This provides effective heat transfer without a circulation pump. With such an external heater, the feed material and catalyst are supplied to the reactor via this heater via line (1—1) along with the recirculating stream.

EXAMPLE

Production of Isosorbide at Nominal 18 Million lbs/Year

Referring to FIG. 1, 45% by weight aqueous sorbitol solution is introduced via line (1) at a rate of 8490 lbs/hr to the simultaneous reaction-separation equipment represented in FIG. 1 as block (50) and shown in detail in FIG. 2. The stream contains about 21 lb-moles of sorbitol and about 259 lb-moles of water. Referring to FIG. 2, aqueous sulfuric acid, 10% by weight, is injected via line (20) at a rate of 200 lb/hr in sufficient quantity to maintain the sulfuric acid concentration at 0.5–0.6 weight % of the sorbitol feed (water-free basis). Heat input to stage heaters (51), (52), and (53) is adjusted to maintain the temperatures at 125, 135, and 145° C., respectively. Pressure in the head-space above the third stage is maintained at about 18 to 20 mm Hg. The dehydration reaction through all the stages forms about 16.8 lb-moles of isosorbide in 80% yield. 4.2 lb-moles of starting sorbitol go to byproducts comprising mostly monomeric monoanhydro sorbitol derivatives, dimers, polymeric materials, and minor amounts of other decomposition products, as well as the acid catalyst.

Isosorbide is recovered via line (2) as a vapor stream with the water evolved in the reaction, while the byproducts and unrecovered isosorbide are removed via line (12). With recycle of the byproducts as described herein, the byproduct stream reaches a steady concentration. Under the steady continuous operating mode, it contains about 28% isosorbide, 58–60% sorbitan isomers, 10–12% water-insoluble polymer, and about 1.4–1.5% by weight sulfuric acid, and is removed via line (12) at a rate of 3270 lbs/hr. The byproduct stream is mixed with 6900 lbs of water via line (13) and the insoluble polymer is allowed to precipitate. It is then fed via line (14) to a filter (90), wherein the precipitated polymer is removed, as a filter cake, at a rate of 370 lbs/hr of polymer, which is washed with part of the water from line (13) and discharged from line (15). The filtrate, containing about 920 lbs/hr isosorbide and 1930 lbs/hr water-soluble byproducts and 50 lbs/hr of the acid catalyst, is discharged via line (16) at a rate of about 9800 lbs/hr. About one-seventh of this stream is purged via line (17). The remainder, about 8400 lbs/hr stream, is supplemented with make-up sulfuric acid at a rate of 7 lbs/hr, as a 50% solution, via line (20) and injected back to the reaction step via line (18) along with fresh sorbitol feed. Thus, it recycles about 790 lbs/hr isosorbide, 1654 lbs/hr byproducts and most of the acid catalyst back to the reaction-separation part of the process.

As a result of the recycle, isosorbide loss is only about the 130 lbs in the purge stream (17) and most of the 2450 lbs/hr isosorbide produced by the dehydration reaction (i.e., 2450−130=2320 lbs/hr) is recovered and removed as vapors, along with the water evolved in the reaction, via line (2). Upon condensation, it produces 18.5 million lbs/year isosorbide, as an aqueous solution. The isosorbide recovery is 2320/2450 or about 95%, and overall process yield to isosorbide is then 76% (95% of 80%), versus 56% obtained without the recycle.

What is claimed is:

1. A process for separating monomeric and dimeric sugar alcohols from a mixture comprising monomeric, dimeric and polymeric sugar alcohols, comprising:
    a) diluting with water a mixture comprising monomeric, dimeric and polymeric sugar alcohols;
    b) allowing most of the polymeric sugar alcohols to precipitate from the diluted mixture obtained in (a); and
    c) separating the precipitated polymeric sugar alcohols from the diluted mixture to obtain a solution of soluble monomeric and dimeric sugar alcohols.

2. The process of claim 1, wherein the monomeric sugar alcohol comprises isosorbide.

3. The process of claim 1, wherein the monomeric, dimeric and polymeric sugar alcohols are derived from an acid-catalyzed dehydration of a sugar alcohol.

4. The process of claim 1 wherein the amount of water used for dilution is 1 to 4 pounds per pound of the mixture comprising monomeric, dimeric and polymeric sugar alcohols.

5. The process of claim 1, further comprising purging a portion of the solution of soluble monomeric and dimeric sugar alcohols.

6. The process of claim 1, further comprising cooling the diluted mixture to near ambient temperature.

7. The process of claim 1, further comprising neutralizing at least a portion of the acid catalyst in the mixture of monomeric, dimeric and polymeric sugar alcohols.

8. A continuous byproducts recycle process for the manufacture of dianhydro sugar alcohols, comprising the steps of:
    a) continuously dehydrating a sugar alcohol in the presence of an acid catalyst to produce a reaction mass comprising monoanhydro sugar alcohols, dianhydro sugar alcohols, dimers, and polymers;
    b) continuously separating a portion of the dianhydro sugar alcohols from the reaction mass to produce a product stream and a byproduct stream;
    c) continuously removing at least a portion of the byproduct stream, said stream comprising mostly monoanhydro sugar alcohol isomers, dimers, polymers and dianhydro sugar alcohol;
    d) diluting the byproducts stream of (c) with water in an amount sufficient to precipitate the polymers;
    e) allowing most of the polymers to precipitate from the diluted mixture of (d);
    f) separating the polymers precipitated in (e) from the dissolved byproducts; and
    g) feeding the dissolved byproducts solution from (f) to the dehydration step of (a); while maintaining the flows in and out of steps (a)–(g) at substantially steady rates and coordinated to maintain substantially steady process conditions.

9. The process of claim 8 wherein the dianhydro sugar alcohol is isosorbide.

10. The process of claim 8 wherein the amount of water used for dilution is 1 to 4 pounds per pound of byproducts.

11. The process of claim 8, further comprising purging a portion of the solution of soluble monomeric and dimeric sugar alcohols.

12. The process of claim 8, further comprising cooling the diluted mixture to near ambient temperature.

13. The process of claim 8, further comprising neutralizing at least a portion of the acid catalyst in the mixture of monomeric, dimeric and polymeric sugar alcohols.

* * * * *